United States Patent
Barteau et al.

(10) Patent No.: US 6,232,504 B1
(45) Date of Patent: May 15, 2001

(54) FUNCTIONALIZED MONOLITH CATALYST AND PROCESS FOR PRODUCTION OF KETENES

(75) Inventors: Mark Barteau, Wilmington; Marylin Huff, Newark, both of DE (US); Uwe Pogodda, Borstel (DE); Ramiro Martinez-Rey, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/473,269

(22) Filed: Dec. 27, 1999

Related U.S. Application Data

(60) Provisional application No. 60/114,027, filed on Dec. 29, 1998.

(51) Int. Cl.⁷ .................................................. C07C 45/87
(52) U.S. Cl. .......................................... 568/301; 568/302
(58) Field of Search ...................................... 568/301, 302

(56) References Cited

U.S. PATENT DOCUMENTS

| | | | |
|---|---|---|---|
| 3,366,689 | * | 1/1968 | Maeda et al. ......................... 568/301 |
| 3,790,620 | * | 2/1974 | Butler et al. . | |
| 5,475,144 | * | 12/1995 | Watson et al. ....................... 568/301 |

OTHER PUBLICATIONS

CA:109:109951 abs of J Organomet Chem by Singh 338(2) by 255–60, 1988.*
CA:107:235774 abs of Can J Chem by Allen 65(8) pp 1719–23, 1987.*

* cited by examiner

*Primary Examiner*—Jean F. Vollano
(74) *Attorney, Agent, or Firm*—Connolly Bove Lodge & Hutz LLP

(57) ABSTRACT

A process to produce ketenes by reacting a carboxylic acid in a reactor in the presence of a silica monolith catalyst. The silica monolith catalyst can be prepared by silanizing the monolith.

8 Claims, 1 Drawing Sheet

FUNCTIONALIZED MONOLITH CATALYST AND PROCESS FOR PRODUCTION OF KETENES

Figure 1:
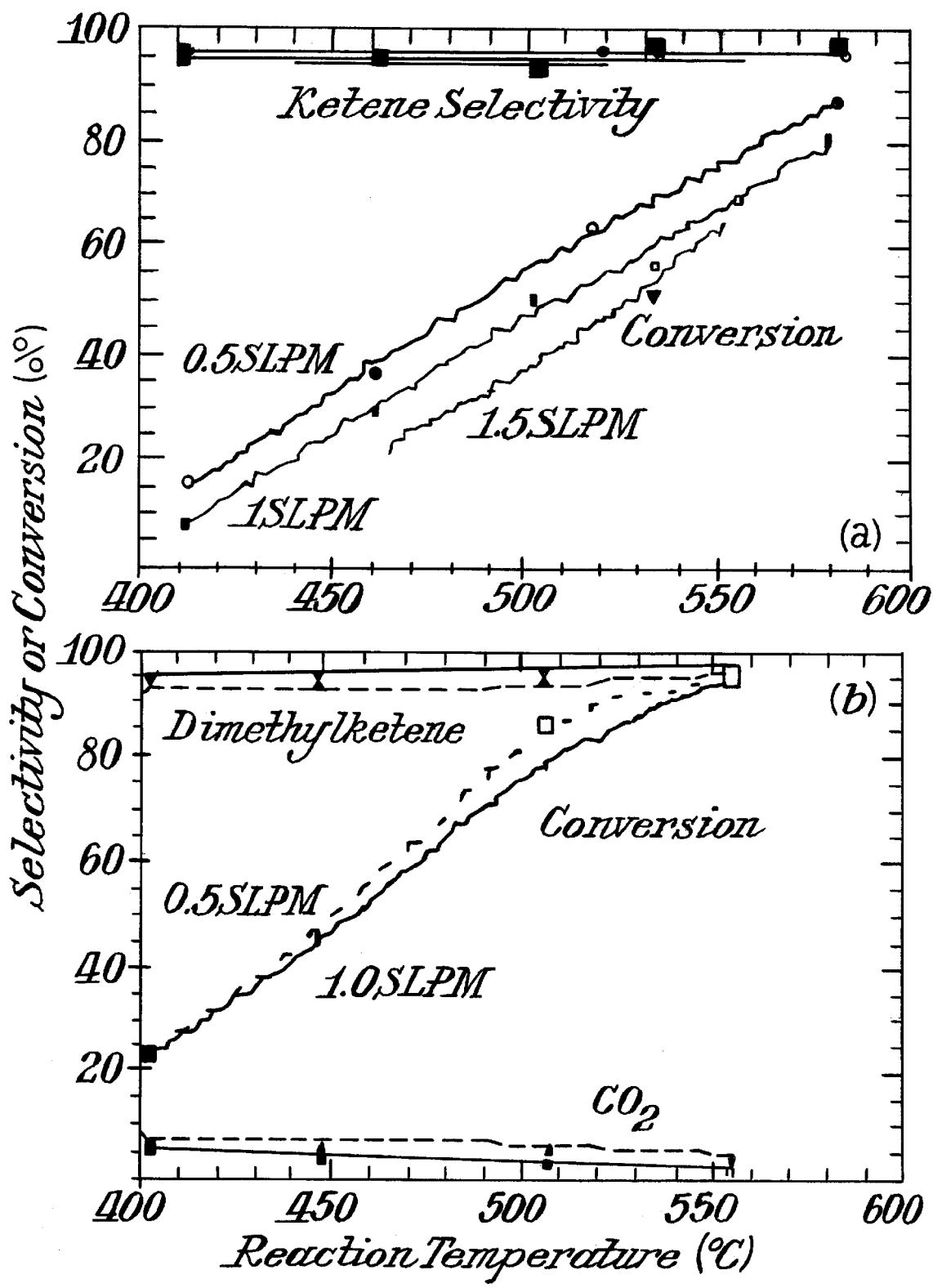

This application is based on Ser. No. 60/114,027 filed Dec. 29, 1998, which is incorporated by reference in its entirety, for all useful purposes.

The United States Government has rights in the invention as provided by National Science Foundation Grant (CTS-94-10965).

BACKGROUND OF THE INVENTION

Ketenes are highly reactive chemical intermediates of the general form $RR'C=C=O$. Ketenes find application as powerful acylating agents for a range of compounds. Alkyl ketene dimers (AKD) are produced from long chain ($C_8-C_{32}$) fatty acids for use as paper sizing agents.

While there exist a variety of routes to ketenes, these do not generally involve heterogeneous catalysis. Low molecular weight ketenes are produced by thermal pyrolysis of carboxylic acids or ketones at 600–800° C. (Encyclopedia of Polymer Science and Technology, Vol. 8, Interscience, New York, (1968), p. 45, Rice, F. O., Greenberg, J., Waters, C. E., Vollrath, R. E., J. Am. Chem. Soc. 56, 1760 (1934), Hurd, C. D. and Roe, A., J. Am. Chem. Soc. 61, 3355 (1939), Hurd, C. D. and Martin, K. E., J. Am. Chem. Soc. 51, 3614 (1929), Bamford, C. H. and Dewar, J. S., J. Chem. Soc., 2877 (1949) and Guenther, W. B. and Walters, W. D., J. Am. Chem. Soc. 81, 1310 (1959)). Higher molecular weight ketenes are produced by dehalogenation of α-halo acyl halides or dehydrohalogenation of acyl halides with tertiary amines as disclosed in U.S. Pat. No. 2,383,863 issued to R. Heuter and U.S. Pat. No. 3,535,383 issued to E. S. Rothman. None of these routes enjoys the efficiency of a catalytic process. The dehalogenation-based processes are multi-step organic syntheses which utilize hazardous reagents, e.g., phosgene, and solvents, and yield undesirable byproducts. Thus efficiency, safety and waste minimization imperatives all favor the development of a one-step catalytic process.

Gun'ko and coworkers (Brei, V. V., Gunko, V. M., Khavryuchenko, V. D., Chuiko, A. A., Kinetics and Catalysis 31, 1019 (1991), Brei, V. V., Gun'ko, V. M. Dudnik, V. V., Chuiko, A. A., Langmuir, 8, (1992), and Gun'ko, V. M., Brei, V. V., Chuiko, A. A., Kinetics and Catalysis 32, 91 (1991)) observed the formation of ketene in temperature programmed desorption "TPD" experiments in which acetic acid and acetyl chloride were employed to synthesize acetoxysilyl groups on aerosils.

U.S. Pat. No. 3,366,689 issued to Maeda et al. describes a process for manufacturing ketenes by contact dehydration for aliphatic carboxylic acids having 3 to 6 carbon atoms with a silica catalyst having a specific surface area of less than 100 m²/g. and at a temperature of 400–900° C. The silica catalyst may be diatomaceous earth, pumice, acid clay, kaolin, aluminum silicate, magnesium silicate or silica-boric oxide.

U.S. Pat. No. 2,175,811 issued to Loder describes a process for preparation of ketene which comprises thermally decomposing lower aliphatic monocarboxylic acid esters in the vapor phase at 500–1000° C. in contact with a catalyst which can be silica gel supporting a promoter such as phosphoric acid or boron oxide.

U.S. Pat. No. 2,295,644 issued to Fallows et al. describes a process for manufacturing ketene and acetic anhydride by thermal dehydration of acetic acid vapors in the presence of a catalyst by passing the vapors at 500–1,000° C. over pumice with zinc oxide or cadmium oxide deposited on the surface.

U.S. Pat. No. 1,870,104 issued to Dreyfus describes a process for the manufacture of ketene, acetic acid or acetic anhydride or mixture thereof which comprises passing vapors of acetic acid and acetaldehyde at 500–600° C. over a catalyst selected from a group which includes pumice.

U.S. Pat. No. 2,108,829 issued to Sixt et al. describes a catalytic process for producing ketene which comprises subjecting acetic acid vapors containing acetic anhydride forming catalyst to heating at a temperature between 500–1000° C. under partial vacuum and immediately separating ketene from the other components. Solid catalysts, such as pea size "carborundum" coated with sodium metaphosphate, may be used (Example 1).

U.S. Pat. No. 5,475,144 issued to Watson et al., describes a catalyst and process for synthesis of ketenes from carboxylic acids. Some of the important features of this catalyst are surface areas of at least 100 m²/gram with a controlled population of hydroxyl groups on the surface. The selectivities disclosed were from 35 to 90% at conversions of 30 to 100%.

One of the difficulties with utilization of high surface area powder catalysts at high flow rates is the large pressure drop across the catalyst bed. We have invented a functionalized monolith catalyst which avoids this problem, and which produces higher product selectivities and yields than the catalysts disclosed in U.S. Pat. No. 5,475,144.

A BRIEF SUMMARY OF THE INVENTION

It is object of this invention to have a more efficient process for producing ketenes.

It is another object of this invention to operate at lower temperatures then described above.

It is another object of this invention to reduce the byproduct formation.

It is another object of this invention to have a process that can produce ketenes in a one-step catalytic process.

It is still a further object of this invention to have a safer process which also involves less waste formation than other processes such as (1) thermal pyrolysis of carboxylic acids or ketones, and (2) dehalogenation of α-halo acyl halides, and (3) dehydrohalogenation of acyl halides with tertiary amines.

We have discovered three basic derivatization methods which give active and selective catalysts.

The ketenes manufactured according to the claimed process are useful in areas such as but not limited to, acylating agents for pharmaceutical and sizing agents (intermediates for alkyl ketene dimers and multimers).

A BRIEF DESCRIPTION OF THE FIGURES

FIGS. 1(a) and 1(b) illustrate the acid conversion and ketene selectivity.

DESCRIPTION OF THE PREFERRED EMBODIMENT

The ketenes can be produced in a reactor system. The reactor system can be batch or continuous. A continuous system is however preferred. The ketenes can be produced in a reactor, preferably a flow reactor containing this catalyst which can be at a temperature of at least about 600 K and preferably from about 700 K to about 1000 K and more preferably from about 750 K to 850 K. The ketenes can be straight chain or branched chain. The pressures could be at an elevated pressure or run in a vacuum.

The selectivities for production of ketenes such as, but not limited to $C_2$–$C_{32}$ ketenes, preferably from $C_2$–$C_{22}$ and most preferably from $C_2$–$C_5$ ketenes, from at least about 65%, preferably from at least about 75% up to about 98% have been achieved.

The catalyst contains of a low surface area reticulated silica monolith (supplied by Vesuvius Hi-Tech Ceramics, Inc.) which is 18 mm in diameter and 10 mm in depth and has a void fraction of 50 to 85% and 30 to 80 pores per linear inch. The physical dimensions of the catalyst can be altered to accommodate other reactor designs. The catalyst is activated by boiling in water for at least 1 hour, and preferably at least about 3 hours, and most preferably at least about 8 hours, and then it is dried preferably in air at temperature of at least about 100° C. and preferably about 120° C. for approximately 2 hours and then derivatized by deposition of other silicon-containing compounds. We have discovered three basic derivatization methods which give active and selective catalysts.

The first way to produce the catalyst is by starting with a high surface area silica (commercially available from BDH) to make a slurry (concentration 20 mg silica/20 ml) with water preferably in excess. The monolith is exposed to the well-stirred slurry for at least 1 hour, and preferably at least about 2 hours, then removed and dried preferably in air for approximately 2 hours at temperature of at least about 100° C. and preferably about 120° C. These times can be shortened by operating at higher temperature or lengthened by operating at lower temperature.

The second way to produce the catalyst is having the monolith silanized by treatment with a liquid silanizing agent such as, but not limited to, tetraethoxysilane (TEOS), $Si(OCH_2CH_3)_4$ for at least 1 hour, and preferably at least about 2 hours, and draining the excess liquid TEOS off the monolith The monolith is then exposed to water vapor for at least about 10 hours, preferably at least about 15 hours, in order to hydrolyze the TEOS. These times can be shortened by operating at higher temperature or lengthened by operating at lower temperature. The monolith is then dried in air as in the first method.

The third way to produce the catalyst is having the monolith silanized by treatment with a silanizing agent such as TEOS in hydrochloric acid solution. The preferred embodiment is a solution of approximately 2:1 by volume of concentrated hydrochloric acid and TEOS that is well mixed at room temperature, and then the monolith is inserted into solution immediately with no further stirring. The monolith is removed after 2 hours and the excess liquid is allowed to drain. The monolith is then dried at 120° C. for 15 hours, and the excess silica dust is blown off at the end of this period using compressed air. These times can be shortened by operating at higher temperature or lengthened by operating at lower temperature.

The last of these methods produces the best catalyst.

EXPERIMENTAL TEST

A cylindrical monolith (having external dimensions of 17 mm; a diameter×10 mm height; 65 pores per linear inch and mass=1.0–2.0 grams) was inserted in a hollow quartz tube which served as the reactor. The monolith was pretreated in a flowing inert gas, preferably helium at a temperature of 673 K for 1 hour and then heated to the desired reaction temperature and exposed to the feed stream. The feed stream consisted of helium at a flow rate of 0.5 to 2 1/min (STP) which was passed through a bubbler containing the acid of interest, before entering the reactor. These flow rates could not be achieved with the powder catalyst of U.S. Pat. No. 5,475,144. In the case of acetic acid, the approximate concentration in the gas feed stream produced in this way was $1.25 \times 10^{-3}$ moles/liter. The product and feed compositions were monitored with a quadruple mass spectrometer.

FIGS. 1(a) and 1(b) illustrate typical results from the dehydration of (a) acetic acid and (b) isobutyric acid over a high surface area $SiO_2$ catalyst supported on a low surface area $SiO_2$ monolith. Experiments were conducted at carrier gas flow rates of 0.5 to 1.5 SLPM that correspond to the contacts ranging from 0.01 to 0.06 seconds. The acid conversion as well as the ketene selectivity are shown in FIGS. 1(a) and 1(b).

Typical performances of catalysts prepared according to recipe #3 above are listed in Tables 1 and 2. Maximum yields of ketene from acetic acid approached 80% (Table 1). Maximum yields achieved with our previous powder catalysts never exceeded 20% for this reaction. We have examined several higher carboxylic acids as well. Results for isobutyric acid (Table 2) show greater than 90% yield of dimethylketene (vs. <75% previously). A comparison between the performance of the $SiO_2$ monolith catalyst and the $SiO_2$ powder catalyst is given in Table 3.

TABLE 1

Typical Results for the Dehydration of Acetic Acid over the Functionalized Silica Monolith

| Flow (slpm) | Temperature (deg C.) | Temperature (K.) | Acetic Acid Conversion | Ketene Selectivity | $CO_2$ Selectivity |
|---|---|---|---|---|---|
| 0.5 | 413 | 686 | 0.16 | 0.97 | 0.03 |
| 0.5 | 461 | 734 | 0.37 | 0.97 | 0.03 |
| 0.5 | 517 | 790 | 0.64 | 0.96 | 0.03 |
| 1 | 411 | 684 | 0.09 | 0.96 | 0.04 |
| 1 | 461 | 734 | 0.30 | 0.96 | 0.04 |
| 1 | 502 | 775 | 0.51 | 0.93 | 0.05 |
| 1 | 533 | 806 | 0.57 | 0.97 | 0.03 |
| 1 | 580 | 853 | 0.81 | 0.98 | 0.02 |
| 1.5 | 416 | 689 | 0.16 | 0.94 | 0.06 |
| 1.5 | 465 | 738 | 0.23 | 0.96 | 0.06 |
| 1.5 | 504 | 777 | 0.40 | 0.95 | 0.04 |
| 1.5 | 533 | 806 | 0.52 | 0.96 | 0.04 |
| 1.5 | 551 | 824 | 0.65 | 0.95 | 0.04 |

TABLE 2

Typical Results for the Dehydration of Isobutyric Acid over the Functionalized Silica Monolith

| Flow (slpm) | Temperature (deg C.) | Temperature (K.) | Isobutyric Acid Conversion | Dimethyl Ketene Selectivity | $CO_2$ Selectivity |
|---|---|---|---|---|---|
| 0.5 | 403 | 676 | 0.24 | 0.93 | 0.07 |
| 0.5 | 447 | 720 | 0.48 | 0.94 | 0.06 |
| 0.5 | 505 | 778 | 0.86 | 0.95 | 0.05 |
| 0.5 | 553 | 826 | 0.96 | 0.96 | 0.04 |
| 1 | 403 | 676 | 0.23 | 0.95 | 0.05 |
| 1 | 447 | 720 | 0.45 | 0.96 | 0.04 |
| 1 | 505 | 778 | 0.79 | 0.96 | 0.04 |
| 1 | 553 | 826 | 0.95 | 0.98 | 0.02 |

TABLE 3

Measured Performance of Monolith and Powder Catalysts for Ketene Synthesis

| | Maximum Yield of Ketene with a Powder Catalyst | Maximum Yield of Ketene with a Monolith Catalyst |
|---|---|---|
| $CH_3COOH \emptyset CH_2CO + H_2O$ | 20% | 80% |
| $(CH_3)_2CHCOOH \emptyset (CH_3)_2CCO + H_2O$ | 75% | 95% |

While there is shown and described herein certain specific structures embodying the invention, it will be manifest to those skilled in the art that various modifications and rearrangements of the parts maybe made without departing from the spirit and scope of the underlying inventive concept and that the same is not limited to the particular forms herein described.

We claim:

1. A process to produce ketenes which comprises reacting a carboxylic acid in a reactor in the presence of a silica functionalized monolith catalyst.

2. The process as claimed in claim 1, wherein the reaction is carried out in a flow reactor at a temperature of at least about 600° K.

3. The process as claimed in claim 1, wherein the reaction is carried out at a temperature between about 700 to about 1,000° K.

4. The process as claimed in claim 1, wherein the reaction is carried out at a temperature between about 750 to about 850° K.

5. The process as claimed in claim 1, wherein the ketene is a $C_2$–$C_{32}$ ketene having a selectivity from at least about 65%.

6. The process as claimed in claim 1, wherein the ketene is a $C_2$–$C_{22}$ ketene having a selectivity from at least about 75%.

7. The process as claimed in claim 1, wherein the ketene is a $C_2$–$C_5$ ketene having a selectivity from at about 75% to about 98%.

8. The process as claimed in claim 1, wherein the monolith catalyst is a silica catalyst.

* * * * *